United States Patent
Besse et al.

(10) Patent No.: US 10,702,294 B2
(45) Date of Patent: Jul. 7, 2020

(54) TOOL FOR A MEDICAL INSTRUMENT, AND MEDICAL INSTRUMENT

(71) Applicant: Karl Storz SE & Co. KG, Tuttlingen (DE)

(72) Inventors: Régis Besse, Le Perray en Yvelines (FR); Yann Thouément, Les Essarts le Roi (FR)

(73) Assignee: Karl Storz SE & Co. KG, Tuttlingen (DE)

( * ) Notice: Subject to any disclaimer, the term of this patent is extended or adjusted under 35 U.S.C. 154(b) by 0 days.

(21) Appl. No.: 15/476,360

(22) Filed: Mar. 31, 2017

(65) Prior Publication Data

US 2017/0296210 A1    Oct. 19, 2017

(30) Foreign Application Priority Data

Apr. 14, 2016 (DE) .......................... 10 2016 106 930

(51) Int. Cl.
*A61B 17/22* (2006.01)
*A61B 17/29* (2006.01)
(Continued)

(52) U.S. Cl.
CPC ........ *A61B 17/22031* (2013.01); *A61B 17/29* (2013.01); *A61B 17/3201* (2013.01);
(Continued)

(58) Field of Classification Search
CPC .......... A61B 17/22031; A61B 17/3201; A61B 17/28; A61B 17/2804; A61B 17/29;
(Continued)

(56) References Cited

U.S. PATENT DOCUMENTS 5,275,615 A * 1/1994 Rose ...................... A61B 17/29
                                                606/207
5,304,185 A   4/1994 Taylor
(Continued)

FOREIGN PATENT DOCUMENTS

DE    4319968 C1    10/1994
DE    10028896 A1   12/2001
(Continued)

OTHER PUBLICATIONS

EP Search Report Application No. 17163573.3 Completed Date: Aug. 10, 2017; dated Aug. 28, 2017 7 pages.
(Continued)

*Primary Examiner* — Sarah A Simpson
(74) *Attorney, Agent, or Firm* — Whitmyer IP Group LLC

(57) ABSTRACT

A tool for a medical instrument includes a stationary component, a branch which is pivotable relative to the stationary component about a pivot axis, a transmission device for transmitting a force to the pivotable branch, and a coupling device for coupling the transmission device to the pivotable branch in such a way that a translation of the transmission device entails a pivoting movement of the pivotable branch about its pivot axis. The coupling device includes several coupling portions on the pivotable branch and several coupling portions on the transmission device. Each coupling portion on the pivotable branch is assigned to a corresponding coupling portion on the transmission device. The coupling portions are arranged and designed such that the coupling of pivotable branch and transmission device is effected, depending on the positions of pivotable branch and transmission device, by different pairs of corresponding coupling portions.

20 Claims, 3 Drawing Sheets

(51) Int. Cl.
*A61B 17/3201* (2006.01)
*A61B 17/3205* (2006.01)
*A61B 90/00* (2016.01)
*A61B 17/00* (2006.01)

(52) U.S. Cl.
CPC ............... *A61B 17/3205* (2013.01); *A61B 2017/00367* (2013.01); *A61B 2017/00477* (2013.01); *A61B 2017/294* (2013.01); *A61B 2017/2936* (2013.01); *A61B 2090/0813* (2016.02)

(58) Field of Classification Search
CPC .. A61B 2017/22034; A61B 2017/2926; A61B 2017/2932; A61B 2017/2933; A61B 2017/2939; A61B 2017/2936; A61B 2017/294; A61B 2017/2941
See application file for complete search history.

(56) References Cited

U.S. PATENT DOCUMENTS 5,507,772 A      4/1996  Shutt et al.
2016/0175001 A1* 6/2016  Hibner ........... A61B 17/320092
                                                        606/28

FOREIGN PATENT DOCUMENTS

WO    2010144219 A1    12/2010
WO    2012051200 A2    4/2012
WO    2012083041 A2    6/2012

OTHER PUBLICATIONS

German Search Report Application No. 10 2016 106 930.2 Completed Date: Feb. 4, 2017; dated Feb. 17, 2017 9 Pages.

* cited by examiner

Fig. 1
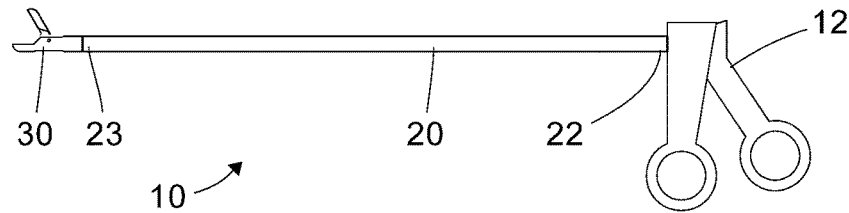
Fig. 2 A-A
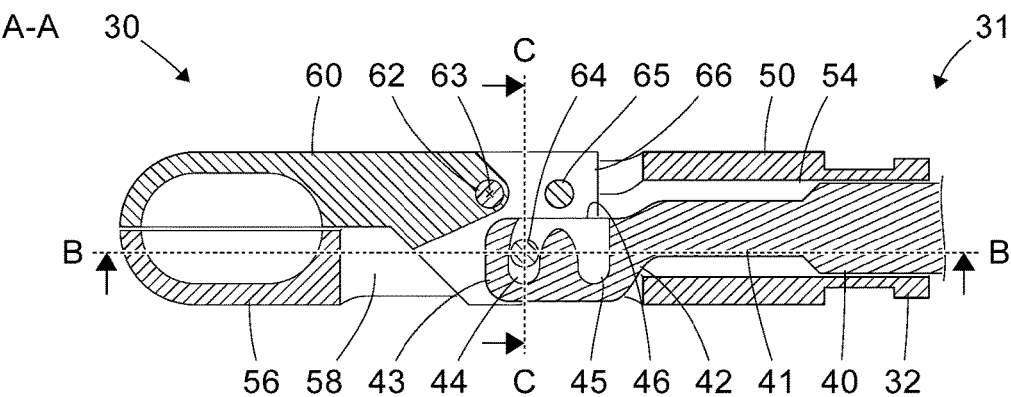
Fig. 3 B-B
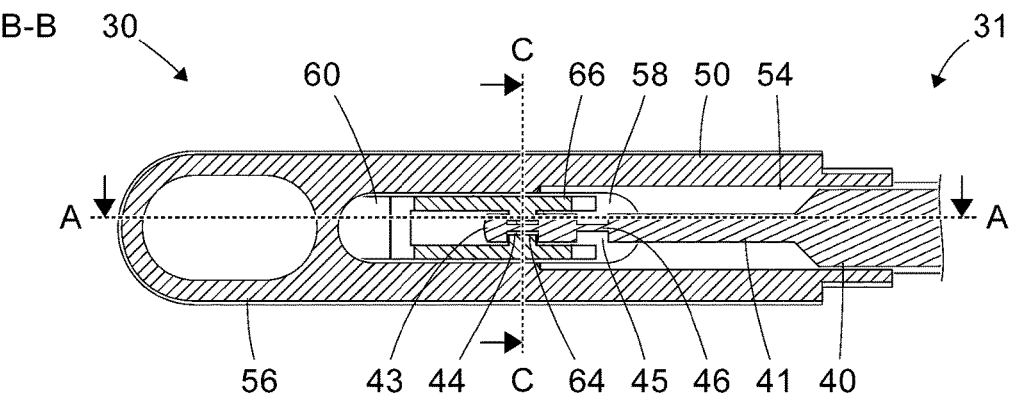
Fig. 4 C-C
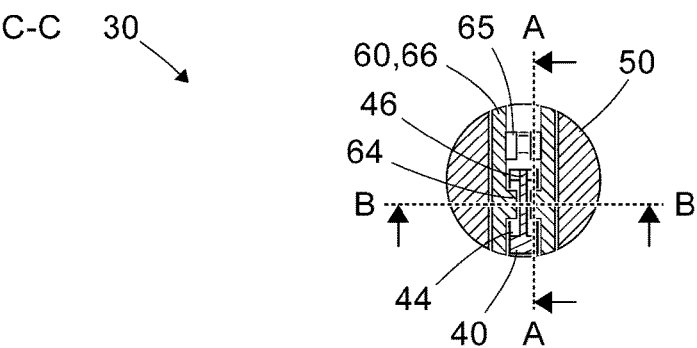

TOOL FOR A MEDICAL INSTRUMENT, AND MEDICAL INSTRUMENT

TECHNICAL FIELD

The present invention relates to a tool for a medical instrument, and to a medical instrument with such a tool. The tool and the medical instrument are provided and designed in particular for microinvasive uses.

BACKGROUND

Particularly in microinvasive uses, medical instruments are becoming ever smaller. To be able to insert the medical instruments through ever smaller accesses, or through thin work channels in other larger medical instruments, their shanks and their tools at the distal ends of the shanks need to have ever smaller cross sections. At the same time, a high-quality medical instrument should be able to be completely cleaned in a simple way and re-used as often as possible. The required mechanical robustness presupposes that the medical instrument has a simple and uncomplicated structure and is composed of the smallest possible number of components.

SUMMARY

It is an object of the present invention to make available an improved tool for a medical instrument and also an improved medical instrument.

This object is achieved by the subject matter of the independent claims.

Developments are set forth in the dependent claims.

A tool for a medical instrument comprises a stationary component, a branch which is pivotable relative to the stationary component about a pivot axis, a transmission device for transmitting a force to the pivotable branch, and a coupling device for coupling the transmission device to the branch in such a way that a translation of the transmission device entails a pivoting movement of the pivotable branch about its pivot axis, wherein the coupling device comprises several coupling portions on the pivotable branch and several coupling portions on the transmission device, wherein each coupling portion on the pivotable branch is assigned to a corresponding coupling portion on the transmission device, and wherein the coupling portions are arranged and designed such that the coupling of pivotable branch and transmission device is effected, depending on the positions of pivotable branch and transmission device, by different pairs of corresponding coupling portions.

The tool is provided and designed in particular for a microinvasive medical instrument. For example, the tool is provided and designed to be coupled to a distal end of a shaft of a microinvasive medical instrument in such a way as to be releasable without destruction, or is designed to be connected thereto permanently, i.e. such that it is not releasable without destruction.

The tool comprises in particular two or more branches or jaw parts, which can be designed for the holding, gripping, squeezing or cutting of tissue. For this purpose, all or several branches of the tool are in particular pivotable relative to each other about one or more pivot axes. If one branch of the tool is designed to be stationary or non-movable or rigid, this branch is in particular part of the stationary component or is designed in one piece with the latter.

The pivot axis about which the pivotable branch is pivotable is in particular defined by a hinge between the pivotable branch and the stationary component. The pivot axis is in particular orthogonal to an intended direction of movement of the transmission device and/or orthogonal to a longitudinal axis of the tool and/or orthogonal to the longitudinal axis of a shaft connected to the tool or of a shaft which is releasably connectable to the tool and is connected in the intended manner. In the case of a curved shaft, the longitudinal axis of the shaft is meant near its distal end.

The stationary component comprises in particular a shaft coupling for the non-destructive releasable mechanical connection of the tool to the distal end of a shaft of a medical instrument or to the distal end of a shaft for a medical instrument.

The transmission device can be provided for transmitting a force and for transmitting a torque. The transmission device comprises in particular a rigid or flexible rod or a rigid or flexible tube. The transmission device is arranged in particular in a shaft connected to the tool or is provided and designed for arrangement in a shaft to be connected to the tool.

The coupling portions on the transmission device are in particular arranged on or near the distal end of the transmission device. The coupling portions on the pivotable branch are in particular provided on an area of the pivotable branch that faces away from the end of the pivotable branch intended to interact with tissue. In particular, at least two or at least three pairs of corresponding coupling portions are provided which couple the pivotable branch to the transmission device in at least two or at least three differs ranges of positions of the pivotable branch and of the transmission device.

The coupling portions on the transmission device are in particular at least partially concave. The coupling portions on the pivotable branch are in particular at least partially convex. Alternatively, the coupling portions on the transmission device can be at least partially convex and the coupling portions on the pivotable branch can be at least partially concave. Alternatively, some of the coupling portions on the transmission device can be concave, while others of the coupling portions on the transmission device are convex, and some of the coupling portions on the pivotable branch can be convex while others of the coupling portions on the pivotable branch can be concave.

The coupling between the transmission device and the branch is effected in particular by the fact that at least one coupling portion on the pivotable branch engages at any time in a corresponding coupling portion on the transmission device and/or a coupling portion on the transmission device engages at any time in a corresponding coupling portion on the pivotable branch. The coupling between the pivotable branch and the transmission device is to this extent by form-fit engagement.

In a tool as described here, the coupling device comprises in particular no connecting rod.

The coupling device of the tool described here allows the transmission device to be coupled to the pivotable branch without a connecting rod. This can make it possible to reduce the number of components of the tool. The reduced number of components can permit larger cross sections of the individual components while maintaining the same external cross section of the tool. Since the coupling is effected by different pairs of corresponding coupling portions at different positions of the pivotable branch, and accordingly different positions of the transmission device, it is moreover possible to adjust the gear ratio or the ratio between torque on the pivotable branch and force on the transmission device. In particular, the dependency of this gear ratio on the position of the pivotable branch can also be adjusted. In particular, an advantageous gear ratio can be adjusted even at a large maximum opening angle between the branches of the tool for each position of the pivotable branch. For this purpose, the distances of the coupling portions, more exactly the distances of the points or lines or surfaces in which corresponding coupling portions touch each other, from the pivot axis are adjusted. A large distance permits a considerable torque on the branch, while a small distance permits a pivoting movement of the pivotable branch about a relatively large angle in a relatively small movement of the transmission device.

In a tool as described here, the coupling portions on the transmission device form in particular a regular or irregular toothed rack in which the coupling portions on the pivotable branch engage like teeth of a toothed wheel.

In a tool as described here, the extreme angle positions of the pivotable branch enclose in particular an angle of at least 90 degrees or of at least 100 degrees or of at least 110 degrees.

In many conventional tools for medical instruments or on medical instruments, the extreme angle positions of the individual pivotable branch enclose an angle of only ca. 60 degrees or ca. 70 degrees. A greater angle between extreme angle positions of the pivotable branch and a correspondingly greater angle of opening can be advantageous in many uses.

In a tool as described here, two adjacent coupling portions on the pivotable branch have, with respect to the pivot axis, in particular an angle distance in the range of 50 degrees to 70 degrees or in the range of 55 degrees to 65 degrees.

In a tool as described here, the angle range within which the coupling between the transmission device and the pivotable branch is effected by a selected pair of corresponding coupling portions has in particular a width in the range of 50 degrees to 70 degrees or in the range of 55 degrees to 65 degrees.

An angle distance or a width of the angle range of ca. 60 degrees can have the effect that, within a pivoting range of the pivotable branch of 120 degrees, the angle between the longitudinal axis of the transmission device, along which the latter is movable, on the one hand, and a straight line through the pivot axis and the coupling portion momentarily providing the coupling between pivotable branch and transmission device, on the other hand, at any time lies in the range between 60 degrees and 120 degrees. The gear ratio-defining distance between a straight line parallel to the direction of movement of the transmission device through the coupling portion on the pivotable branch providing the coupling, on the one hand, and the pivot axis of the pivotable branch, on the other hand, then varies by not more than the ratio 1:sin(60 degrees)=1:0.87.

In a tool as described here, a coupling portion on the transmission device comprises in particular a groove or a slit in the transmission device.

In particular, each coupling portion on the transmission device comprises a groove or a slit in the transmission device. The groove or the slit or the grooves or slits are in particular arranged on or near the distal end of the transmission device.

Each groove or each slit extends in particular in a direction orthogonal or substantially orthogonal to the intended direction of movement of the transmission device. Each groove or each slit on the transmission device can be straight or substantially straight or curved. In particular, one groove or one slit is straight and one groove or one slit is curved. For example, a first groove is straight, and a second groove arranged in the distal direction from the first groove is curved toward the first groove; or a first slit is straight, and a second slit arranged in the distal direction from the first slit is curved toward the first slit.

In a tool as described here, a coupling portion on the pivotable branch comprises in particular a peg or a pin or a rod-shaped portion.

In particular, each coupling portion on the pivotable branch comprises peg or a pin or a rod-shaped portion.

In a tool as described here, one coupling portion or each coupling portion on the pivotable branch comprises in particular a groove or a slit in the pivotable branch.

In a tool as described here, one coupling portion or each coupling portion on the transmission device comprises in particular a peg or a pin or a rod-shaped portion on the transmission device.

In a tool as described here, two coupling portions designed as pegs are in particular in each case arranged opposite each other on the pivotable branch, wherein two coupling portions designed as grooves are in each case arranged opposite each other on the transmission device.

The coupling portions designed as pegs are in particular arranged facing each other on two mutually facing surfaces of two wall-shaped areas of the pivotable branch, wherein the transmission device is arranged between the wall-shaped areas of the pivotable branch. In particular, two coupling portions designed as pegs are in each case arranged and designed in mirror symmetry with respect to a plane of symmetry, wherein the plane of symmetry is at the same time the plane of symmetry of the transmission device.

Coupling portions designed as grooves on the transmission device are in particular formed on sides of the transmission device directed away from each other and in surfaces of the transmission device directed away from each other. Two coupling portions designed as grooves are in each case arranged in particular in mirror symmetry with respect to a plane of symmetry, wherein the plane of symmetry is in particular at the same time the plane of symmetry of the pivotable branch.

In a tool as described here, the coupling portions are in particular arranged in pairs and in mirror symmetry with respect to a plane of symmetry.

In particular, all of the coupling portions are arranged in pairs and in mirror symmetry with respect to a plane of symmetry.

A symmetrical arrangement of coupling portions can permit guiding of the transmission device or of the distal end thereof in a corresponding gap in the branch or, conversely, can permit guiding of the branch in a gap in the distal end of the transmission device. This guiding can reduce play and improve the mechanical robustness of the tool.

In a tool as described here, a wall is in particular arranged between mutually opposite grooves on the transmission device.

Even a thin wall between mutually opposite grooves directed away from each other can considerably increase the mechanical strength of the transmission device in the area of the coupling device. The wall can permit the transmission of greater forces between transmission device and pivotable branch.

In a tool as described here, two coupling portions are in each case arranged opposite each other on the pivotable branch, wherein two coupling portions are in each case arranged opposite each other on the transmission device.

Coupling portions arranged opposite each other on the branch are in particular directed toward each other and arranged on mutually facing surfaces of the branch. Coupling portions arranged opposite each other on the branch are in particular arranged in mirror symmetry with respect to a plane of symmetry, wherein the plane of symmetry can at the same time be the plane of symmetry of the transmission device.

Coupling portions arranged opposite each other on the transmission device are in particular directed away from each other on surfaces of the transmission device facing away from each other. Coupling portions arranged opposite each other on the transmission device are in particular arranged in mirror symmetry with respect to a plane of symmetry, wherein the plane of symmetry can at the same time be the plane of symmetry of the pivotable branch.

In a tool as described here, the transmission device has in particular a cranked portion near its distal end.

The cranked portion permits an arrangement of the coupling portions on the transmission device asymmetrically with respect to the longitudinal axis or to the axis which in the proximal direction from the cranked portion is the axis of symmetry of the transmission device. In particular, the longitudinal axis of the transmission device or the axis which in the proximal direction from the cranked portion is the axis of symmetry of the transmission device is arranged between the coupling portions on the transmission device and the pivot axis of the pivotable branch. This can permit an improvement the gear ratio or, with the same force on the transmission device, can permit a greater torque on the pivotable branch.

In a tool as described here, the stationary component has in particular a channel, wherein the outer contour of the cross section of the transmission device, in the area provided for arrangement in the channel, and the inner contour of the cross section of the channel are designed in such a way that the transmission device is guided in the channel with little play and little friction, wherein the channel is formed by a structural element which is arranged in a cavity of the stationary component, and wherein the cross section of the cavity is greater than the cross section of the transmission device.

The structural element is in particular at least partially sleeve-shaped or tubular. The formation of the channel in a structural element which, in the production of the tool, can be attached only later to the stationary component can make it easier, even possible, to insert a transmission device with a cranked portion. In particular, in the production of the tool, the distal end of the transmission device is firstly guided from the proximal direction through the cavity of the stationary component and coupled to the pivotable branch. As a result of the cross section of the cavity being greater than the cross section of the transmission device, the transmission device can be pivoted or tilted in the cavity in order to couple the coupling portions at the distal end of the transmission device to the corresponding coupling portions on the pivotable branch. Only then can the structural element forming the channel be attached to the stationary component of the tool from the proximal direction. Thereafter, the channel in the structural element guides the transmission device with little play, in such a way that the coupling between the transmission device and the pivotable branch can no longer be canceled as long as the structural element forming the channel is connected to the stationary component.

A medical instrument comprises a tool as described here, and a shaft which is connected or can be connected to the proximal end of the tool.

BRIEF DESCRIPTION OF THE DRAWINGS

Embodiments are explained in more detail below with reference to the attached figures, in which:

FIG. 1 shows a schematic view of a medical instrument;
FIG. 2 shows a schematic sectional view of a tool for a medical instrument;
FIG. 3 shows a further schematic sectional view of the tool from FIG. 2;
FIG. 4 shows a further schematic sectional view of the medical tool from FIGS. 2 and 3.

DETAILED DESCRIPTION

Figure 5:
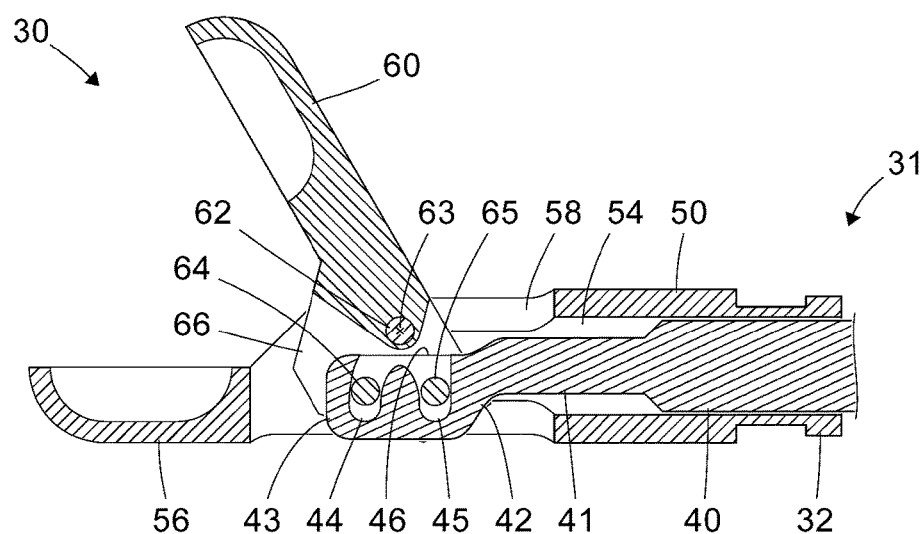
FIG. 5 shows a further schematic sectional view of the tool from FIGS. 2 to 4.

FIG. 1 shows a schematic view of a medical instrument 10 with a manipulation device 12, a shaft 20 and a tool 30. The proximal end 22 of the shaft 20 is mechanically connected to the manipulation device 12 in such a way as to be releasable without destruction, or it is connected thereto permanently, i.e. such that it is not releasable without destruction. The distal end 23 of the shaft 20 is mechanically connected to the tool 30 in such a way as to be releasable without destruction, or it is connected thereto permanently, i.e. such that it is not releasable without destruction.

A transmission device which is not visible from the outside, and which is therefore not shown in FIG. 1, is arranged in the shaft 20. The transmission device couples a manually movable part of the manipulation device 12 to the tool 30. The transmission device is provided and designed to transmit a force and optionally a torque between the manipulation device 12 and the tool 30.

The shaft 20 can be straight or, in contrast to the view in FIG. 1, curved, and it can be rigid or flexible.

FIG. 2 shows a schematic view of a cross section through a tool 30. The tool 30 can be a constituent part of the medical instrument 10 shown in FIG. 1. Alternatively, the tool 30 can be provided to be connected to a distal end of a shaft permanently, i.e. such that it is not releasable without destruction, or to be connected thereto in such a way as to be releasable without destruction, in order to form a medical instrument. The section plane A-A shown in FIG. 2 is parallel to the longitudinal axis of a shaft that is connected or is to be connected to the tool 30 or, in the case of a curved shaft, is parallel to the longitudinal axis thereof at the distal end thereof. The positions of two further section planes B-B and C-C are indicated in FIG. 2.

At its proximal end 31, the tool 30 has a coupling 32 for releasable mechanical connection to a distal end of a shaft in order to form a medical instrument. The coupling 32 is designed, for example, for a bayonet connection.

The tool 30 moreover comprises a transmission device 40, of which the distal end area is arranged in the tool 30 and is shown in FIG. 2. The transmission device 40 has a portion 41 of reduced cross section, which is adjoined by a cranked portion 42. In the distal direction from the cranked portion 42, and as far as its distal end 43, the transmission device is substantially plate-shaped or has the shape of a rectangular parallelepiped. In the example shown, the transmission device 40 is also substantially plate-shaped in the area of the portion 41 of reduced cross section, and corners in the area of the cranked portion 42 and at the distal end 43 are rounded. The plate or the shallow rectangular parallelepiped, of which the outline can be considered as the portion 41, the crank 42 and the area of the transmission device 40 between the cranked portion 42 and the distal end 43, extends parallel or substantially parallel to the section plane A-A of FIG. 2.

Near its distal end 43, the transmission device 40 has two parallel first grooves 44 which are arranged in mirror symmetry and of which only one is directed toward the viewer and therefore visible in the view in FIG. 2. Moreover, near its distal end 43 and in the proximal direction from the first grooves 44, the transmission device 40 has two parallel second grooves 45 which are arranged in mirror symmetry to each other and of which only one is directed toward the viewer and therefore visible in the view in FIG. 2. Between the two parallel and mutually symmetrically arranged first grooves 44 and between the two parallel and mutually symmetrically arranged second grooves 45, a wall 46 is arranged which extends parallel to the section plane A-A of FIG. 2. The first grooves 44 and the second grooves 45 also extend in each case parallel or substantially parallel to the section plane A-A of FIG. 2. The section plane A-A of FIG. 2 intersects one of the two first grooves, namely the first groove 44 directed toward the viewer, and one of the two second grooves, namely the second groove 45 directed toward the viewer.

The tool 30 moreover comprises a stationary component 50 with a continuous bore 54. In the example shown, the stationary component 50 also forms the coupling 32 at the proximal end 31 of the tool 30 and a stationary branch 56. The stationary branch 56 is not movable, in particular not pivotable, relative to the proximal end 31 of the tool 30 and to a shaft mechanically connected to the tool 30 in the intended manner. The stationary component 50 is composed of a small number of structural elements, in particular only two or three, joined rigidly to one another.

The distal end area of the transmission device 40 shown in FIG. 2, or a part thereof, is arranged in the continuous bore in the stationary component 50. The outer contour of the cross section of the transmission device 40, in the proximal direction from the portion 41 of reduced cross section, and the inner contour of the cross section of the continuous bore 54 in the stationary component 50 are designed such that the transmission device 40 is guided in the stationary component 50 with little play and little friction. In particular, the transmission device 40 is movable relative to the stationary component 50 only in a direction parallel to its longitudinal axis and to the section plane A-A, within a predetermined range. The longitudinal axis of the transmission device 40 is in particular the axis of symmetry to which the transmission device 40, in the proximal direction from the portion 41 of reduced cross section, is rotationally symmetrical, and/or the straight line on which the centers of gravity of the cross-sectional surfaces of the transmission device 40 lie in an area that proximally adjoins the portion 41 of reduced cross section.

The transmission device 40 and the continuous bore 54 of the stationary component 50 are in particular designed (for example in each case as circular cylinders) such that the transmission device 40 would be rotatable about its longitudinal axis relative to the stationary component 50 if the coupling described below to a further component of the tool 30 did not prevent this. Alternatively, the transmission device 40 and the stationary component 50, in particular the continuous bore 54, can be designed, for example, with non-rotationally symmetrical cross sections, such that the transmission device 40 is not rotatable relative to the stationary component 50.

The tool 30 moreover comprises a pivotable jaw part or a pivotable branch 60, which is connected pivotably to the stationary component 50 by a hinge 62. The hinge 62 defines a pivot axis 63 orthogonal to the longitudinal axis of the transmission device 40 and orthogonal to the section plane A-A of FIG. 2. The hinge 62 is formed, for example, by a shaft that extends orthogonally with respect to the section plane A-A of FIG. 2.

The pivotable branch 60 is pivotable relative to the stationary component 50 within a predetermined angle range about the pivot axis 63. The predetermined angle range extends between two extreme angle positions of the pivotable branch 60. One extreme angle position of the pivotable branch 60 is shown in FIG. 2. In this extreme angle position of the pivotable branch 60, the latter bears on the stationary branch 56 of the stationary component 50.

The branch 60 has two first pegs 64, lying opposite each other and arranged in mirror symmetry with respect to each other, and two second pegs 65, lying opposite each other and arranged in mirror symmetry with respect to each other, on two substantially parallel and substantially plane and mirror-symmetrical plate-shaped or wall-shaped portions 66. The section plane A-A of FIG. 2 is arranged between the plate-shaped portions 66 of the pivotable branch 60 such that it intersects one of the two first pegs 64 and one of the two second pegs 65. The other first peg 64 and the other second peg 65 are concealed in the view in FIG. 2. In the example shown, the pegs 64, 65 on the pivotable branch 60 each have circular cross sections.

The pivotable branch 60, in particular the plate-shaped areas 66 of the pivotable branch 60, and the area of the transmission device 40 between the cranked portion 42 and its distal end 43 are arranged in a slit 58 in the stationary component 50. In the example shown, the slit 58 is designed as a narrow and elongate continuous bore or as a narrow and elongate countersink that extends parallel to the section plane A-A of FIG. 2.

In the position of the transmission device 40 as shown in FIG. 2, and in the depicted position of the pivotable branch 60, the first pegs 64 on the plate-shaped areas 66 of the pivotable branch 60 engage in the first grooves 44 in the transmission device 40. In other positions of the transmission device 40 and corresponding other positions of the pivotable branch 60, the second pegs 65 on the plate-shaped areas 66 of the pivotable branch 60 alternatively or additionally engage in the second grooves 45 on the transmission device 40.

The cross sections and positions of the grooves 44, 45 on the transmission device 40 and of the pegs 64, 65 on the pivotable branch 60 are adapted to each other such that the transmission device 40 and the pivotable branch 60 are at any time coupled with little play and little friction. Each linear movement of the transmission device 40 parallel to its longitudinal axis thus entails a pivoting movement of the pivotable branch 60 about the pivot axis 63 thereof.

In the example shown, the second grooves 45 are straight at least in parts, whereas the first grooves 44 are curved toward the second grooves 45. The grooves 44, 45 thus form coupling portions (i.e. substantially concave coupling portions) on the transmission device 40, and the pegs 64, 65 form coupling portions (i.e. substantially convex coupling portions) on the pivotable branch 60. The grooves 44, 45 as coupling portions on the transmission device 40 and the pegs 64, 65 as coupling portions on the pivotable branch 60 together form a coupling device for coupling the transmission device 40 to the pivotable branch 60.

FIG. 3 shows a schematic view of a cross section along the plane B-B shown in FIG. 2 through the tool 30 from FIG. 2. The section plane B-B is parallel to the longitudinal axis of the transmission device 40 and orthogonal to the section plane A-A of FIG. 2. The position of the section plane A-A of FIG. 2 is indicated in FIG. 3.

The plate-shaped areas 66 of the pivotable branch 60, and the area of the transmission device 40 situated near the distal end thereof and comprising the grooves 44, 45, are arranged in the slit 58, which extends orthogonally with respect to the section plane B-B of FIG. 3. The transmission device 40 is arranged between the plate-shaped areas 66 of the pivotable branch 60.

The section plane B-B intersects the first pegs 64 on the plate-shaped areas 66 of the pivotable branch 60. The first pegs 64 are arranged opposite each other and in mirror symmetry to each other, such that they protrude toward each other. The first pegs 64 on the pivotable branch 60 engage in the first grooves 44 on the transmission device 40. In the situation shown in FIG. 3, and in the direction of viewing of FIG. 3, the second pegs 65 are concealed and are therefore not shown. The two second grooves 45 on the transmission device 40 are arranged parallel to each other and in mirror symmetry to each other. Provided between the two first grooves 44 and between the two second grooves 45 is the wall 46, which increases the strength of the transmission device in the area of the grooves 44, 45, especially for pulling and pushing forces parallel to the longitudinal axis of the transmission device 40.

FIG. 4 shows a schematic view of a cross section along a plane C-C through the tool 30 shown in FIGS. 2 and 3. The section plane C-C is orthogonal to the longitudinal axis of the transmission device 40, orthogonal to the section plane A-A of FIG. 2, and orthogonal to the section plane B-B of FIG. 3. The position of the section plane C-C is indicated in FIGS. 2 and 3.

The section plane C-C of FIG. 4 intersects both plate-shaped areas 66 of the pivotable branch 60, the first grooves 44 on the transmission device 40 and the first pegs 64 on the plate-shaped areas 66 of the pivotable branch 60. The second pegs 65 on the plate-shaped areas 66 of the pivotable branch 60 lie outside the section plane C-C of FIG. 4 and are discernible in the background. In the example shown, the thickness of the wall 46 between the grooves 44 is smaller than the depth of the grooves 44.

FIG. 5 shows a further schematic view of a cross section through the tool 30 shown in FIGS. 2 to 4. The section plane of FIG. 5 corresponds to the section plane A-A of FIG. 2.

FIG. 5 shows a situation or configuration of the tool 30 that differs from the situation shown in FIGS. 2 to 4. In particular, the transmission device 40 has moved in the distal direction in relation to the situation shown in FIGS. 2 to 4, and the pivotable branch 60 has moved away from the stationary branch 56 on the stationary component 50 as a result of a pivoting movement about the pivot axis 63. In the situation shown in FIG. 5, the first pegs 64 on the pivotable branch 60 engage in the first grooves 44 on the transmission device 40, and the second pegs 65 on the pivotable branch 60 also engage in the second grooves 45 on the transmission device.

Figure 6:
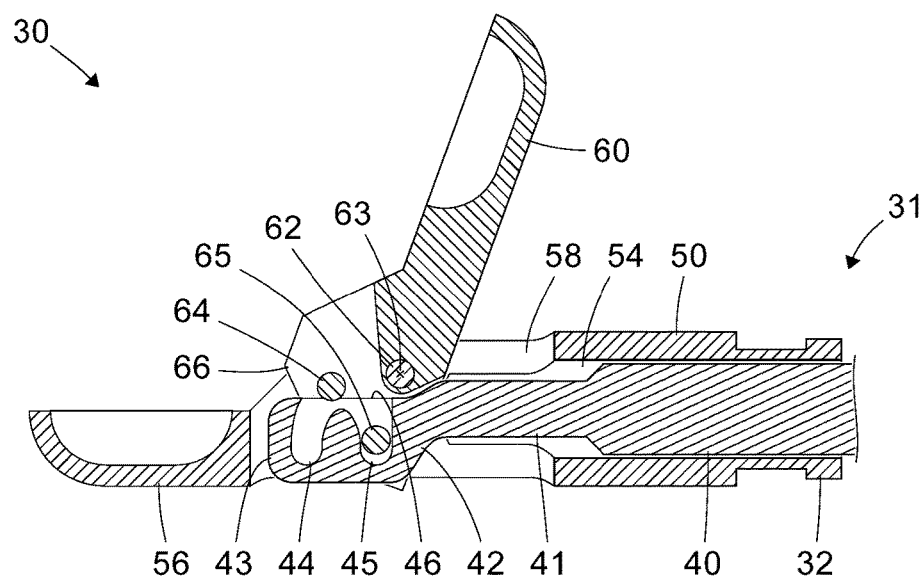
FIG. 6 shows a further schematic sectional view of the tool from FIGS. 2 to 5.

FIG. 6 shows a schematic view of a cross section through the tool 30 shown in FIGS. 2 to 5. The section plane of FIG. 6 corresponds to the section plane A-A of FIG. 2 and to the section plane of FIG. 5.

The situation or configuration shown in FIG. 6 differs from the situations shown in FIGS. 2 to 5 in that the transmission device 40 has moved farther in the distal direction in relation to the position shown in FIG. 5, and the pivotable branch 60 has pivoted farther clockwise about its pivot axis 63 in relation to the position shown in FIG. 5 and has thus moved farther away from the stationary branch 56 on the stationary component 50. In the situation shown in FIG. 6, only the second pegs 65 on the plate-shaped areas 66 of the pivotable branch 60 engage in the second grooves 45 on the transmission device 40.

The angle position of the pivotable branch 60 as shown in FIG. 6 is the extreme position of the pivotable branch 60 away from the position shown in FIG. 2.

Figure 7:
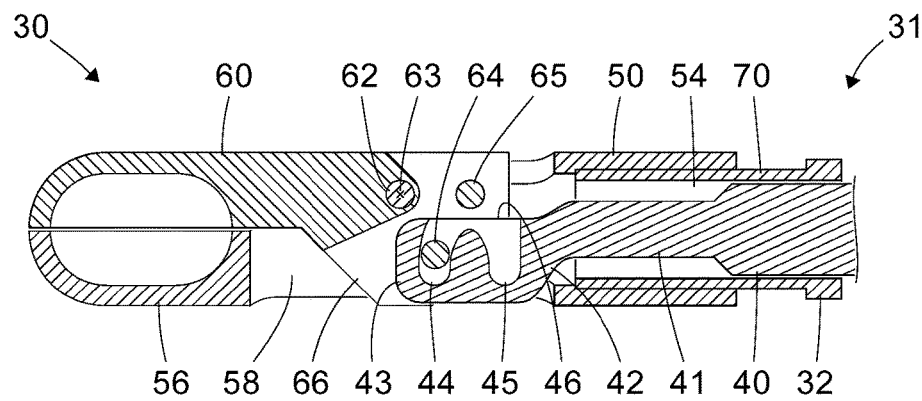
FIG. 7 shows a schematic sectional view of a further tool.

FIG. 7 shows a schematic view of a cross section through a further tool 30 of a medical instrument or for a medical instrument. The section plane of FIG. 7 corresponds to the section plane A-A of FIG. 2 and the section planes of FIGS. 5 and 6. The tool 30 shown in FIG. 7 is similar, in some features, properties and functions, to the tool shown in FIGS. 2 to 6. The situation or configuration shown in FIG. 7 corresponds to the situation shown in FIGS. 2 to 4.

The tool 30 shown in FIG. 7 differs from the tool shown in FIGS. 2 to 6 in particular in that the stationary component 50 is composed of several structural elements. In particular, the proximal end 31 of the tool 30 with the coupling 32 is formed by a structural element 70. Except for the coupling 32 in particular, the structural element 70 is substantially tubular or sleeve-shaped and encloses the continuous bore 54 of the stationary component 50. The inner surface of the structural element 70 thus forms the surface of the continuous bore 54 on which the transmission device 40 bears and which guides the transmission device 40 with little play and little friction. The structural element 70 is produced separately from the rest of the stationary component 50 and, after production of the coupling between the transmission device 40 and the pivotable branch 60 (according to the description of FIG. 8), is placed onto the rest of the stationary component 50 and joined thereto, for example by laser welding.

Figure 8:
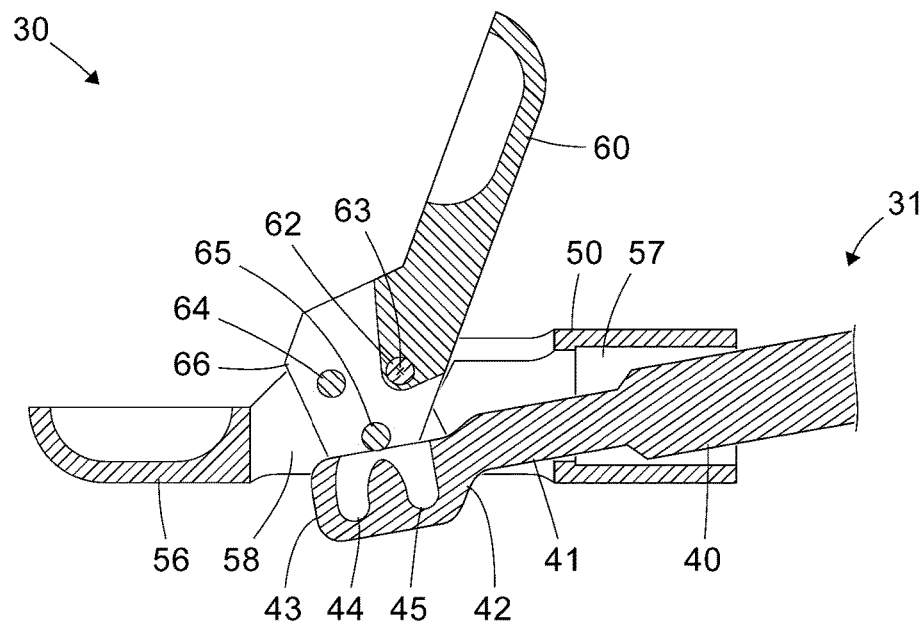
FIG. 8 shows a further schematic sectional view of the tool from FIG. 7.

FIG. 8 shows a further schematic view of a cross section through the tool 30 shown in FIG. 7. The section plane of FIG. 8 corresponds to the section plane of FIG. 7.

FIG. 8 shows a situation or configuration during the assembling of the tool 30. The structural element 70 described with reference to FIG. 7 has not yet been placed on the rest of the stationary component 50. A cavity 57 in the stationary component 50 has a cross section which is much greater than the cross section of the continuous bore 54 in the structural element 70 (cf. FIG. 7). Thus, in the situation shown in FIG. 8, the transmission device 40 is not yet guided with little play in the stationary component 50. The transmission device 40 is therefore tiltable, about an axis orthogonal to the longitudinal axis of the transmission device 40, relative to the stationary component 50 within a predetermined range that is defined by the cross sections of the transmission device 40 and of the cavity 57 in the stationary component 50.

The considerable play of the transmission device 40 in the cavity 57 in the stationary component 50 allows the transmission device 40 to be inserted from the proximal direction into the cavity 57 in the stationary component 50 and allows the distal end 43 and the cranked portion 42 of the transmission device 40 to be guided all the way through the cavity 57 in the stationary component 50. Moreover, the considerable play or the mobility of the transmission device 50 in the cavity 57 in the stationary component 50 permits a tilting of the transmission device 40 as far as the position shown in FIG. 8.

From the position of the transmission device 40 shown in FIG. 8, it can be moved to its intended position shown in FIG. 7, wherein the second pegs 65 on the plate-shaped areas 66 of the pivotable branch 60 are inserted into the second grooves 45 on the transmission device 40. A situation can thus be produced which corresponds to the one shown in FIG. 6 or also to the one shown in FIG. 5 and in which the transmission device 40 and the pivotable branch 60 are coupled by form-fit engagement of the first pegs 64 in the first grooves 44 and/or of the second pegs 65 in the second grooves 45.

Thereafter, the structural element 70 of the stationary component 50 (cf. FIG. 7) can be inserted from the proximal direction into the cavity 57 and joined to the rest of the stationary component 50 in order to produce the situation shown in FIG. 7.

The tools shown in FIGS. 2 to 8 can be varied in many ways. For example, it is possible to provide third pegs for engagement in corresponding third grooves, fourth pegs for engagement in corresponding fourth grooves, etc.

Moreover, the transmission device 40 and the pivotable branch 60 do not have to be designed with mirror symmetry. In particular, grooves 44, 45 and pegs 64, 65 can be provided on opposite sides at different places and for coupling in different angle ranges. Moreover, grooves 44, 45 can be provided only on one side of the transmission device 40, and pegs 64, 65 can be provided only on a plate-shaped area 66 of the pivotable branch 60. The second plate-shaped area 66 can in this case be omitted.

Moreover, it is possible for only one plate-shaped area 66 to be provided on the pivotable branch 60. On this plate-shaped area 66, pegs 64, 65 can be provided only on one side, or pegs 64, 65 can be provided on two sides facing away from each other. The distal end area of the transmission device 40 can engage like a fork around the plate-shaped area 66 of the pivotable branch 60. In this case, grooves 44, 45 are provided on one or on both limbs of the distal end area of the transmission device 40, on the surface areas directed toward each other.

Moreover, as an alternative or as an addition to one or more grooves 44, 45 on the transmission device 40 and corresponding pegs 64, 65 on the pivotable branch 60, it is possible to provide one or more grooves in the pivotable branch 60 and a corresponding number of corresponding pegs on the transmission device 40.

Moreover, it is possible to provide two or more pivotable branches 60 which can in each case be coupled to the transmission device 40 by form-fit engagement of coupling portions on the transmission device 40 and coupling portions on each individual pivotable branch 60.

The invention claimed is:

1. A tool for a medical instrument, with:
a stationary component;
a branch which is pivotable relative to the stationary component about a pivot axis;
a transmission device for transmitting a force to the pivotable branch;
a coupling device for coupling the transmission device to the pivotable branch in such a way that a translation of the transmission device entails a pivoting movement of the pivotable branch about its pivot axis;
wherein the coupling device comprises several coupling portions on the pivotable branch and several corresponding coupling portions on the transmission device,
wherein each coupling portion on the pivotable branch is assigned to one of the corresponding coupling portions on the transmission device;
wherein two coupling portions on the pivotable branch each comprise a peg or a pin or a rod-shaped portion, arranged opposite each other on the pivotable branch, protruding parallel to the pivot axis and lateral to the transmission device, two corresponding coupling portions designed as grooves or slits are arranged opposite each other on the transmission device;
wherein coupling of the pivotable branch and the transmission device is effected by one pair of the coupling portions and one pair of the corresponding coupling portions when the pivotable branch is in a first extreme angle position, and a different pair of the coupling portions and a different pair of the corresponding coupling portions when the pivotable branch is in a second extreme angle position.

2. The tool according to claim 1, in which each of the coupling portions are arranged in pairs and in mirror symmetry with respect to a plane of symmetry.

3. The tool according to claim 1, in which a wall is arranged between the opposite grooves on the transmission device.

4. The tool according to claim 1, in which the transmission device has a cranked portion near its distal end.

5. The tool according to claim 1, in which the stationary component has a channel, the outer contour of the cross section of the transmission device, in the area provided for arrangement in the channel, and the inner contour of the cross section of the channel are designed in such a way that the transmission device is guided in the channel with little play and little friction, the channel is formed by a structural element which is arranged in a cavity of the stationary component, the cross section of the cavity is greater than the cross section of the transmission device.

6. The tool according to claim 1, wherein each of the coupling portions extends parallel to the pivot axis.

7. The tool according to claim 1, wherein the grooves are directed away from each other.

8. The tool according to claim 1, where the first and second extreme angle positions are at an angle of at least 90 degrees with respect to each other.

9. The tool according to claim 8, where the first and second extreme angle positions are at an angle of at least 110 degrees with respect to each other.

10. A medical instrument comprising:
a tool having:
a stationary component;
a branch which is pivotable relative to the stationary component about a pivot axis;
a transmission device for transmitting a force to the pivotable branch;
a coupling device for coupling the transmission device to the pivotable branch in such a way that a translation of the transmission device entails a pivoting movement of the pivotable branch about its pivot axis;
wherein the coupling device comprises several coupling portions on the pivotable branch and several corresponding coupling portions on the transmission device;
wherein two corresponding coupling portions designed as grooves are arranged opposite each other on the transmission device and separated by a wall extending in the direction of the translation;
wherein each coupling portion on the pivotable branch is assigned to one of the corresponding coupling portions on the transmission device;
wherein coupling of the pivotable branch and the transmission device is effected by one pair of the coupling portions and one pair of the corresponding coupling portions when the pivotable branch is in a first extreme angle position, and a different pair of the coupling portions and a different pair of the corresponding coupling portions when the pivotable branch is in a second extreme angle position;

a shaft, which is connected or can be connected to the proximal end of the tool.

11. The medical instrument according to claim 10, wherein each of the coupling portions extends parallel to the pivot axis.

12. The medical instrument according to claim 10, where the first and second extreme angle positions are at an angle of at least 110 degrees with respect to each other.

13. The medical instrument according to claim 10, wherein the shaft is mechanically connected to the tool in such a way as to be releasable without destruction.

14. The medical instrument according to claim 13, wherein the mechanical connection comprises a bayonet connection.

15. A tool for a medical instrument, with:
a stationary component;
a branch which is pivotable relative to the stationary component about a pivot axis;
a transmission device for transmitting a force to the pivotable branch;
a coupling device for coupling the transmission device to the pivotable branch in such a way that a translation of the transmission device entails a pivoting movement of the pivotable branch about its pivot axis;
wherein the coupling device comprises several coupling portions on the pivotable branch and several corresponding coupling portions on the transmission device;
wherein two corresponding coupling portions on the transmission device are separated by a wall extending parallel to the translation;
wherein each coupling portion on the pivotable branch is assigned to one of the corresponding coupling portions on the transmission device;
wherein two coupling portions on the pivotable branch comprise a peg or a pin or a rod-shaped portion, extending axially to the pivot axis; and
wherein the coupling of the pivotable branch and the transmission device is effected by one pair of the coupling portions and one pair of the corresponding coupling portions when the pivotable branch is in a first extreme angle position, and a different pair of the coupling portions and a different pair of the corresponding coupling portions when the pivotable branch is in a second extreme angle position.

16. The tool according to claim 15, wherein each corresponding coupling portion on the transmission device extends in a direction orthogonal to an intended direction of movement of the transmission device.

17. The tool according to claim 15, wherein two of the corresponding coupling portions on the transmission device are differently shaped.

18. The tool according to claim 15, wherein each of the corresponding coupling portions on the transmission device narrows the transmission device.

19. The tool according to claim 15, where the first and second extreme angle positions are at an angle of at least 90 degrees with respect to each other.

20. The tool according to claim 19, where the first and second extreme angle positions are at an angle of at least 110 degrees with respect to each other.

* * * * *